US010881844B2

(12) United States Patent
Besen et al.

(10) Patent No.: US 10,881,844 B2
(45) Date of Patent: Jan. 5, 2021

(54) SYSTEMS FOR PRODUCING AN AEROSOL AND RELATED METHODS OF USE

(71) Applicant: L'Oreal, Paris (FR)

(72) Inventors: Richard Besen, New York, NY (US); Zane Bowman Allen Miller, Seattle, WA (US)

(73) Assignee: L'Oreal, Paris (FR)

( * ) Notice: Subject to any disclaimer, the term of this patent is extended or adjusted under 35 U.S.C. 154(b) by 32 days.

(21) Appl. No.: 15/942,304

(22) Filed: Mar. 30, 2018

(65) Prior Publication Data

US 2019/0298980 A1 Oct. 3, 2019

(51) Int. Cl.

| | |
|---|---|
| ***A61M 35/00*** | (2006.01) |
| ***A45D 34/00*** | (2006.01) |
| ***A45D 40/00*** | (2006.01) |
| ***A61M 11/00*** | (2006.01) |
| ***A61M 15/00*** | (2006.01) |

(52) U.S. Cl.

CPC .......... *A61M 35/003* (2013.01); *A45D 34/00* (2013.01); *A45D 40/00* (2013.01); *A61M 11/00* (2013.01); *A61M 15/0085* (2013.01); *A45D 2034/005* (2013.01); *A45D 2200/057* (2013.01); *A61M 11/005* (2013.01); *A61M 15/0003* (2014.02); *A61M 2202/04* (2013.01); *A61M 2205/0294* (2013.01); *A61M 2205/128* (2013.01); *A61M 2205/33* (2013.01); *A61M 2205/3561* (2013.01); *A61M 2205/50* (2013.01); *A61M 2205/60* (2013.01); *A61M 2205/6054* (2013.01); *A61M 2205/8206* (2013.01)

(58) Field of Classification Search

CPC ...................... A61M 35/003; A61M 15/0085; A61M 11/00; A61M 2205/60; A61M 2202/04; A61M 2205/50; A61M 2205/33; A61M 2205/8206; A61M 2205/0294; A61M 2205/6054; A61M 2205/3561; A61M 2205/128; A61M 15/0003; A61M 11/005; A61M 35/25; A45D 40/00; A45D 34/00; A45D 2200/057; A45D 2034/005

See application file for complete search history.

(56) References Cited

U.S. PATENT DOCUMENTS

| | | | | |
|---|---|---|---|---|
| 6,419,166 B1 * | 7/2002 | Brzezinski | A46B 11/066 | 222/395 |
| 6,851,626 B2 * | 2/2005 | Patel | A61M 15/0065 | 128/200.16 |
| 7,954,486 B2 * | 6/2011 | Papania | A61M 15/0085 | 128/200.14 |

(Continued)

FOREIGN PATENT DOCUMENTS

| | | |
|---|---|---|
| EP | 2987520 A1 | 2/2016 |
| EP | 2996748 A1 | 3/2016 |
| WO | 2014184006 A1 | 11/2014 |

OTHER PUBLICATIONS

International Search Report and Written Opinion, dated Jun. 3, 2019, issued in International Application No. PCT/US2019/023231, filed Mar. 20, 2019, 13 pages.

(Continued)

*Primary Examiner* — Qingzhang Zhou

(74) *Attorney, Agent, or Firm* — Christensen O'Connor Johnson Kindness PLLC

(57) ABSTRACT

Systems for producing an aerosol and related methods of use are described.

18 Claims, 9 Drawing Sheets

(56) References Cited

U.S. PATENT DOCUMENTS

| | | | | |
|---|---|---|---|---|
| 8,430,338 | B2 | 4/2013 | Duru et al. | |
| 8,556,191 | B2 | 10/2013 | Duru et al. | |
| 8,746,586 | B2 | 6/2014 | Duru et al. | |
| 9,095,676 | B2 * | 8/2015 | Gallem | A61M 15/0036 |
| 2002/0129812 | A1 | 9/2002 | Litherland et al. | |
| 2015/0097047 | A1 * | 4/2015 | Hu | B05B 12/081<br>239/4 |
| 2016/0331106 | A1 | 11/2016 | Khormaei | |
| 2017/0050203 | A1 | 2/2017 | Watanabe | |
| 2018/0169682 | A1 | 6/2018 | Miller et al. | |
| 2018/0177957 | A1 | 6/2018 | Streeter et al. | |
| 2018/0280233 | A1 | 10/2018 | Aragon | |
| 2018/0280633 | A1 | 10/2018 | Miller et al. | |

OTHER PUBLICATIONS

International Preliminary Report on Patentability dated Oct. 15, 2020, for International Patent Application No. PCT/US2019/023231, 7 pages.

* cited by examiner

SYSTEMS FOR PRODUCING AN AEROSOL AND RELATED METHODS OF USE

SUMMARY

In an aspect, the present disclosure provides a system comprising a nebulizing body including at least one electro-mechanical nebulizing element; and a replaceable cartridge including one or more fluid reservoirs, and a valve in fluid communication with the one or more fluid reservoirs. In some embodiments, the nebulizing body is configured to releaseably receive the replaceable cartridge.

This forgoing summary is provided to introduce a selection of concepts in a simplified form that are further described below in the Detailed Description. This summary is not intended to identify key features of the claimed subject matter, nor is it intended to be used as an aid in determining the scope of the claimed subject matter.

Figure 1A:
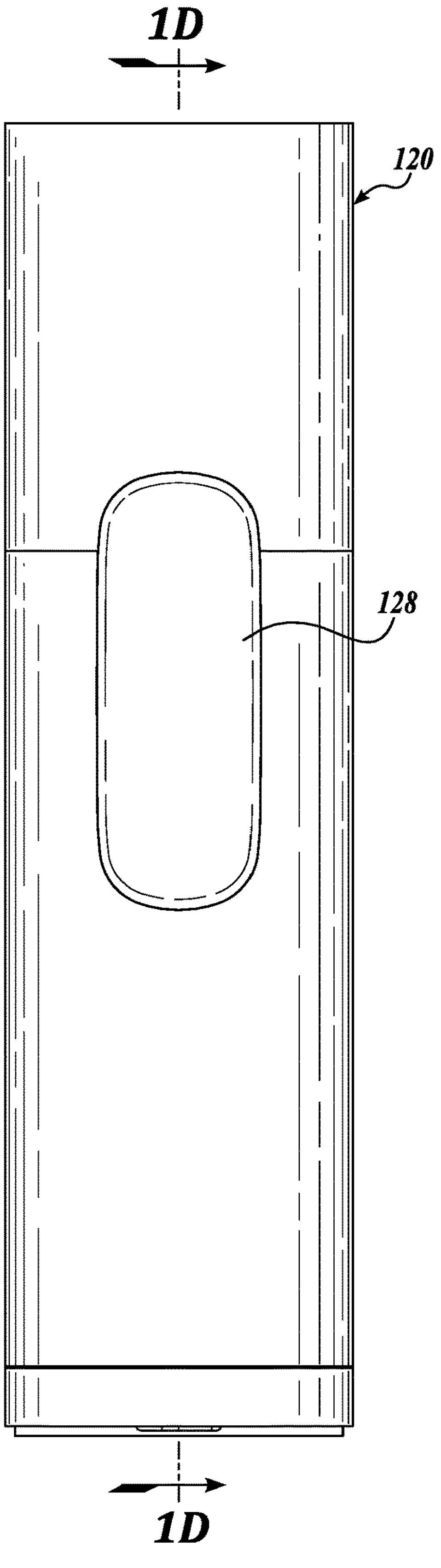
FIG. 1A is a front view of a system in accordance with an embodiment of the disclosure.

Aspects and many of the attendant advantages of the claimed subject matter will become more readily appreciated as the same become better understood by reference to the following detailed description, when taken in conjunction with the accompanying drawings.

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

DETAILED DESCRIPTION

Described herein are systems and methods for delivery of formulations in aerosol form onto skin. Certain conventional nebulizers couple with a cartridge containing a formulation for application onto skin. It would be advantageous to be able to use sequentially many cartridges containing various formulations with a single nebulizing body. However, many conventional nebulizers do not adjust the operation of nebulizing components according to specific characteristics of a formulation disposed in a cartridge coupled thereto, such as formulation viscosity. Accordingly, during operation such conventional nebulizers may fail to convert all or some of the formulation from a liquid to a mist of fine droplets, for example, because they provide insufficient power to the nebulizing components.

Further, many conventional nebulizers couple with cartridges containing formulations for application onto the skin in a way that permanently opens the cartridge. In this regard, formulation remaining in the cartridge may leak from one or more portions of the cartridge when the cartridge is uncoupled from the nebulizer. Accordingly, a user cannot replace a first cartridge that is not completely empty with another cartridge without remaining formulation leaking from the first cartridge. Additionally, any such remaining formulation maybe altered by, for example, exposure to air due to permanently opening the cartridge, thus rendering it unsuitable for future use.

To that end, the following discussion provides examples of systems including a nebulizing body including at least one electro-mechanical nebulizing element; and a replaceable cartridge including one or more fluid reservoirs; and a valve in fluid communication with the one or more fluid reservoirs, wherein the nebulizing body is configured to releaseably receive the replaceable cartridge. As will be described in more detail below, in an embodiment the valve is in a closed state when the replaceable cartridge is not received by and engaged with the nebulizing body. In that regard, a formulation disposed with the fluid reservoir will not leak or otherwise leave the fluid reservoir when the replaceable cartridge is not received by and engaged with the nebulizing body. Additionally, as discussed further herein, in an embodiment, the systems described herein include discharge aerosol circuitry operably coupled to the at least one electro-mechanical nebulizing element and configured to generate a discharge aerosol responsive to one or more inputs indicative of a replaceable cartridge identification. In this regard, in an embodiment the systems described herein are configured to operate the electro-mechanical nebulizing element according to a formulation disposed within the fluid reservoir to discharge an aerosol therefrom.

In the following description, numerous specific details are set forth in order to provide a thorough understanding of one or more embodiments of the present disclosure. It will be apparent to one skilled in the art, however, that many embodiments of the present disclosure may be practiced without some or all of the specific details. In some instances, well-known process steps have not been described in detail in order not to unnecessarily obscure various aspects of the present disclosure. Further, it will be appreciated that embodiments of the present disclosure may employ any combination of features described herein.

Figure 1B:
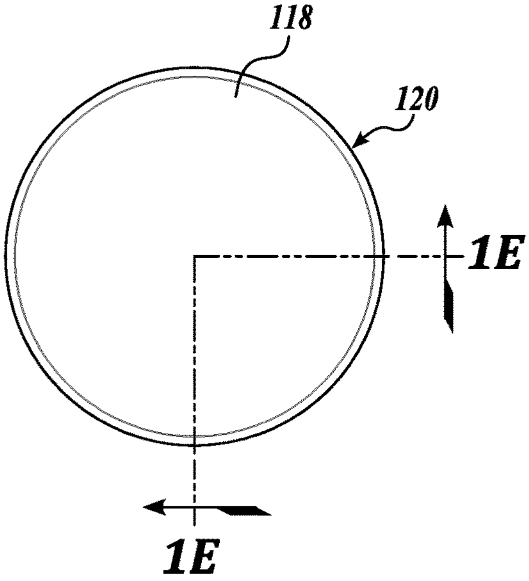
FIG. 1B is a top plan view of the system of FIG. 1A.
Figure 1C:
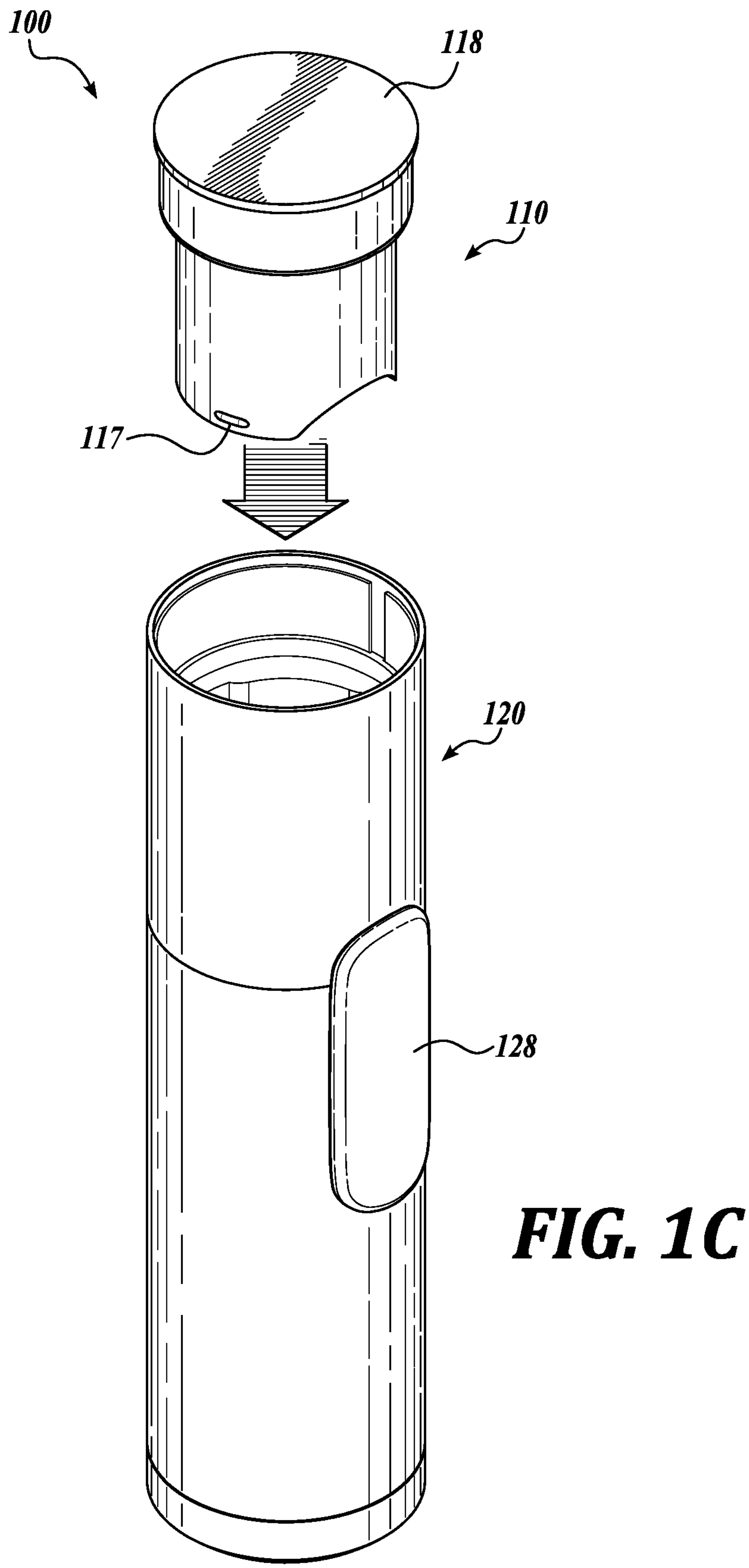
FIG. 1C is a partially-exploded perspective view of the system of FIG. 1A.
Figure 1D:
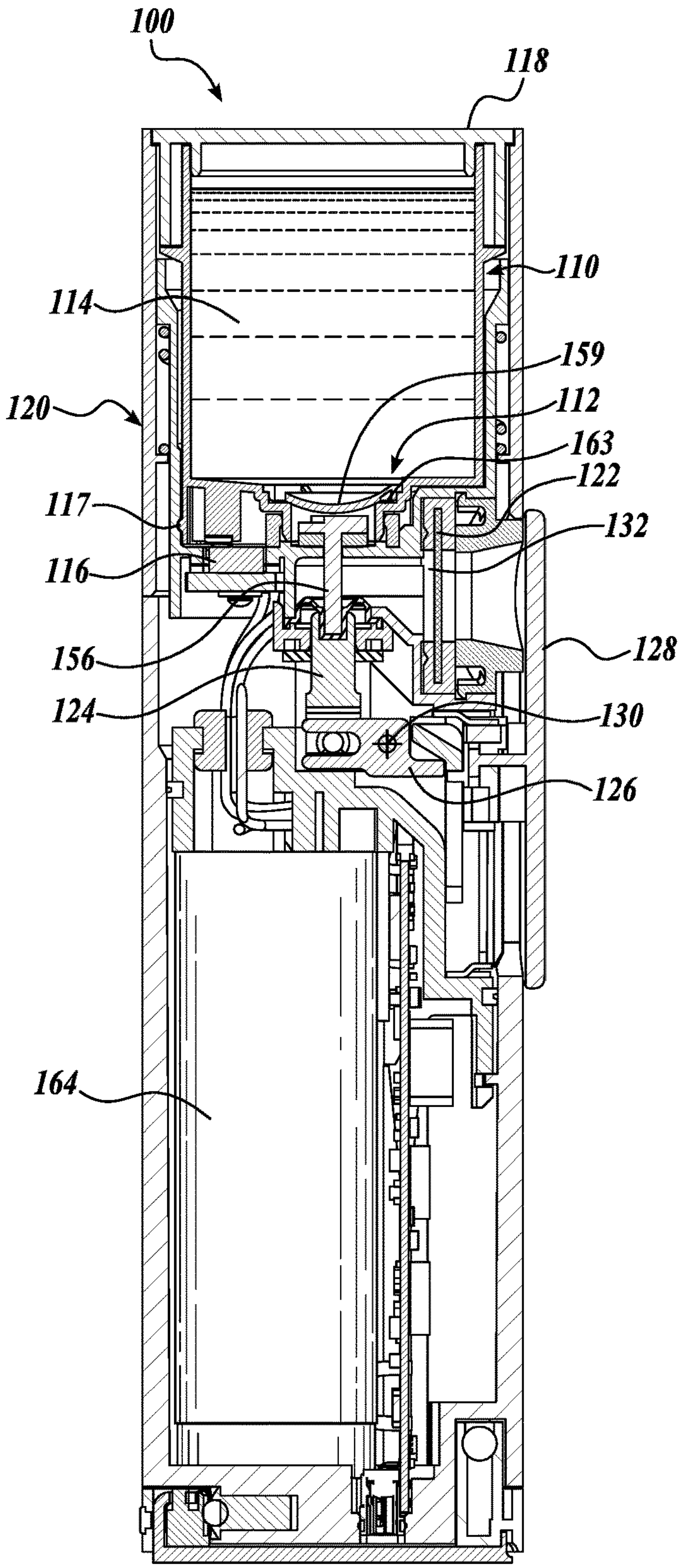
FIG. 1D is a cross-sectional view of the system of FIG. 1A taken along lines 1D-1D in FIG. 1A.

FIG. 1A is a front view of a system 100 in accordance with an embodiment of the disclosure. FIG. 1B is a top plan view of the system 100 of FIG. 1A. FIG. 1C is a partially-exploded perspective view of the system 100 of FIG. 1A. FIG. 1D is a cross-sectional view of the system 100 of FIG. 1A taken along lines 1D-1D in FIG. 1A. As shown in FIGS. 1A-1D, an embodiment of system 100 includes a nebulizing body 120 including a nebulizing assembly 122. The system

100 further includes a replaceable cartridge 110 including a fluid reservoir 114 and a valve 112 in fluid communication with the fluid reservoir 114. FIG. 1C is a partially-exploded view of the system 100 illustrating one embodiment of the replaceable cartridge 110 uncoupled from nebulizing body 120.

As illustrated in FIGS. 1A, 1B, 1D, and 1E, the replaceable cartridge 110 is releaseably received by the nebulizing body 120. As used herein, the replaceable cartridge 110 is releaseably received by the nebulizing body when the replaceable cartridge 110 is securely but removably coupled to the nebulizing body 120. In this regard and as discussed further herein, the replaceable cartridge 110 is releaseably received by the nebulizing body 120 such that the replaceable cartridge 110 can be securely coupled to and subsequently released by the nebulizing body 120 one or more times. In an embodiment, the replaceable cartridge 110 includes one or more detents 117 and the nebulizing body 120 includes detent-receiving structures, or vice versa, both of which are configured to cooperatively and removeably couple the replaceable cartridge 110 and the nebulizing body 120. Of course, the system 100 can include other cooperatively-coupling structures, such as threads configured to removeably couple the replaceable cartridge 110 and the nebulizing body 120.

In an embodiment, the nebulizing body 120 is configured to releaseably receive the replaceable cartridge 110 without engaging with the releasable cartridge 100, thus leaving the valve 112 in a closed state, as illustrated in FIG. 1D. As used herein, the replaceable cartridge 110 is engaged with the nebulizing body 120 when the valve 112 is in an open state and the fluid reservoir 114 of the replaceable cartridge 110 is in fluid communication with the nebulizing assembly 122. Accordingly, the valve 112 is in a closed state when the replaceable cartridge 110 is not engaged with the nebulizing body 120. Thus, when the replaceable cartridge 110 is not engaged with the nebulizing body 120, the fluid reservoir 114 is not coupled in fluid communication with the nebulizing assembly 122. In this regard, the replaceable cartridge 110 in an unengaged configuration is received by the nebulizing body 120 and, accordingly, the valve 112 is in a closed state, as illustrated FIGS. 1D and 1E.

Figure 2A:
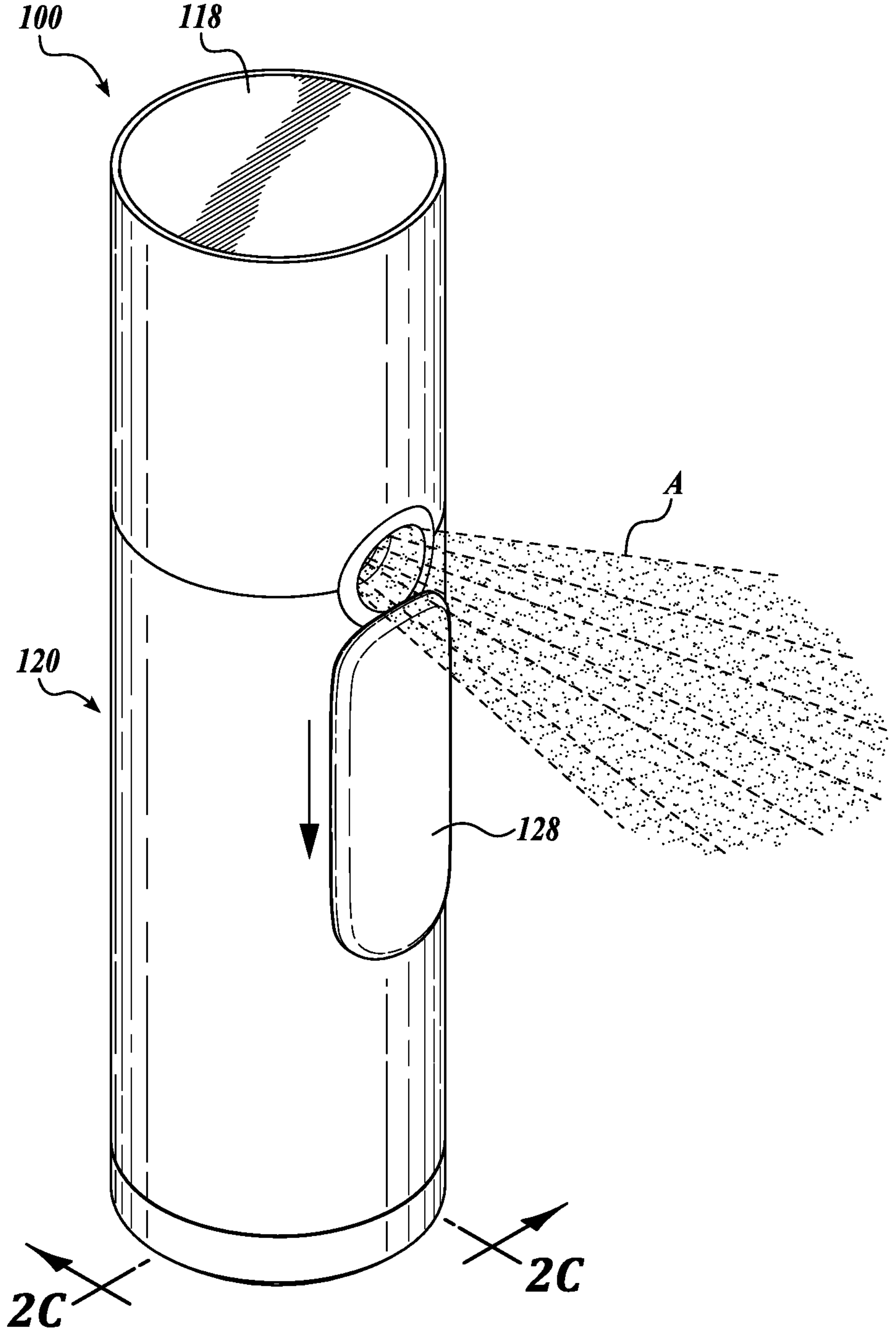
FIG. 2A is a perspective view of the system of FIG. 1C showing an aerosol discharged from the system.
Figure 2B:
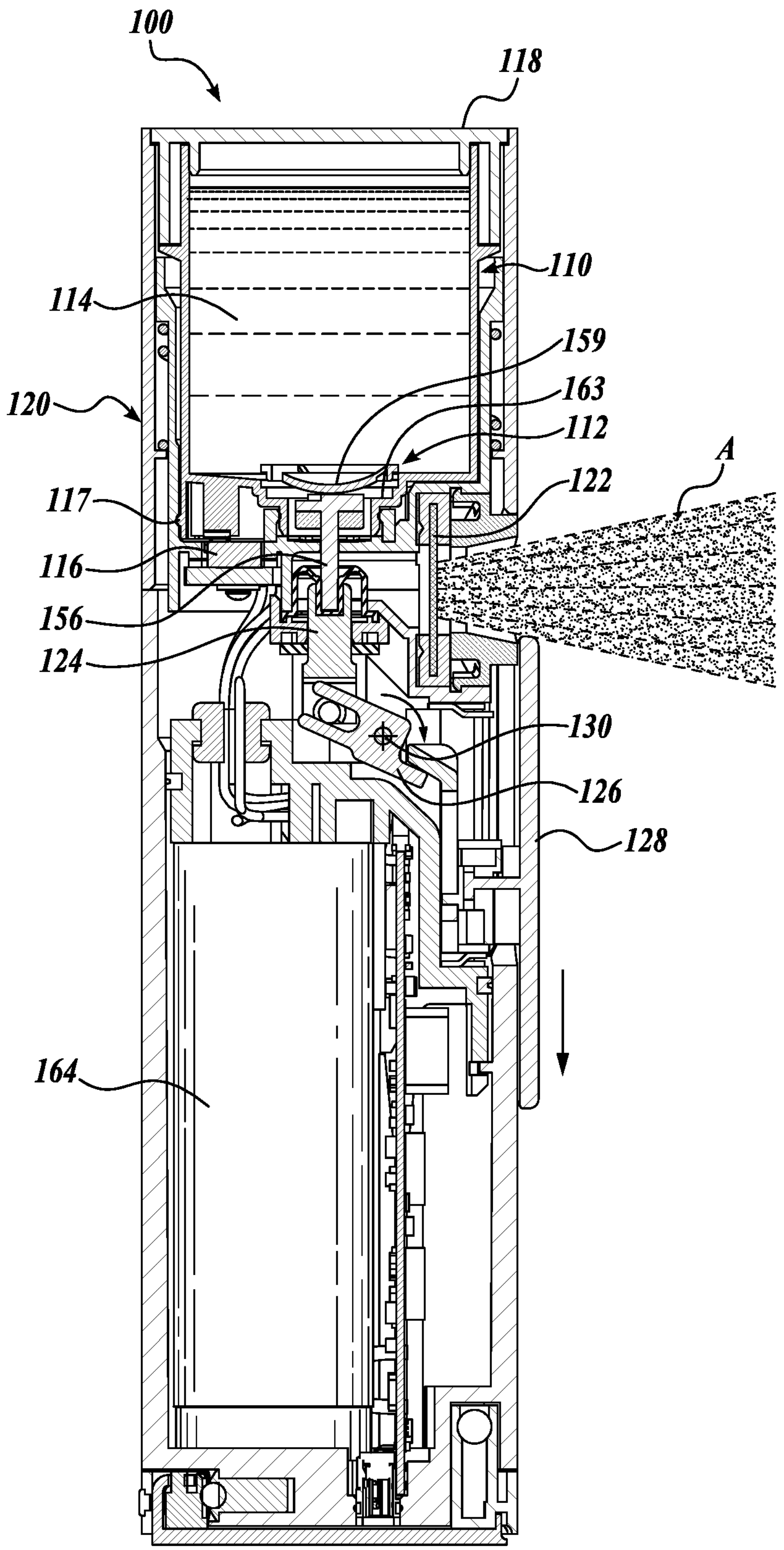
FIG. 2B is another cross-section view of the system of FIG. 1A taken along the lines 1D-1D in FIG. 1B showing an aerosol discharged from the system as a result of switch actuation.
Figure 2C:
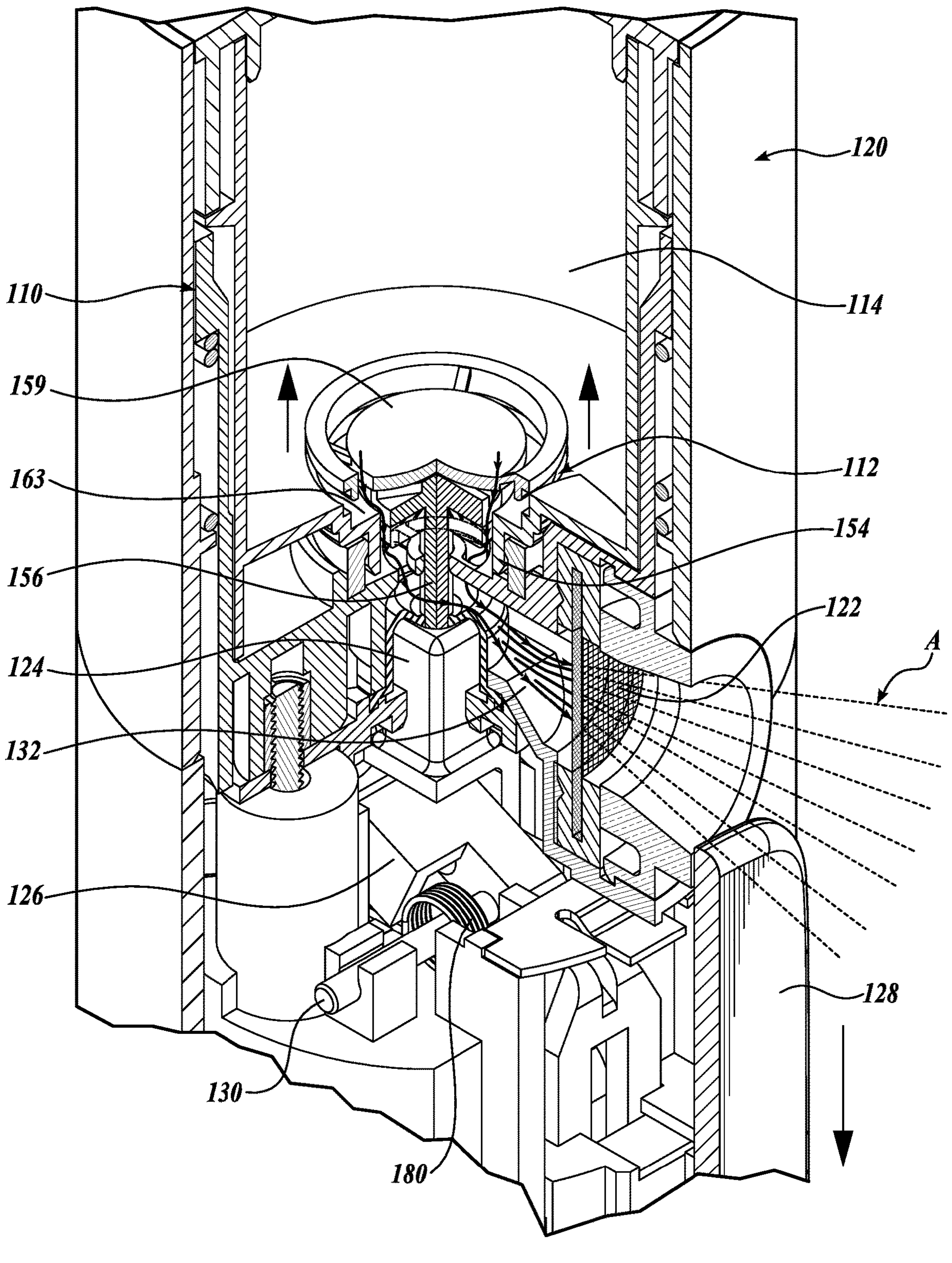
FIG. 2C is an isometric cutaway view of the system of FIG. 2B taken along lines 2C-2C in FIG. 2A.

Alternatively, the valve 112 is in an open state and the fluid reservoir 114 is coupled in fluid communication with the at least one nebulizing assembly 122 when the replaceable cartridge 110 is received by and engaged with the nebulizing body 120. In this regard, attention is directed to FIGS. 2A, 2B, and 2C, in which a configuration of the system 100 according to embodiments of the disclosure is illustrated. Referring to FIGS. 2B and 2C, the replaceable cartridge 110 is shown releaseably received by the nebulizing body 120 by detents 117. In order to be engaged, the nebulizing body 120 in some embodiments includes an actuatable switch 128 configured to selectively place the valve 112 in an open state.

Figure 1E:
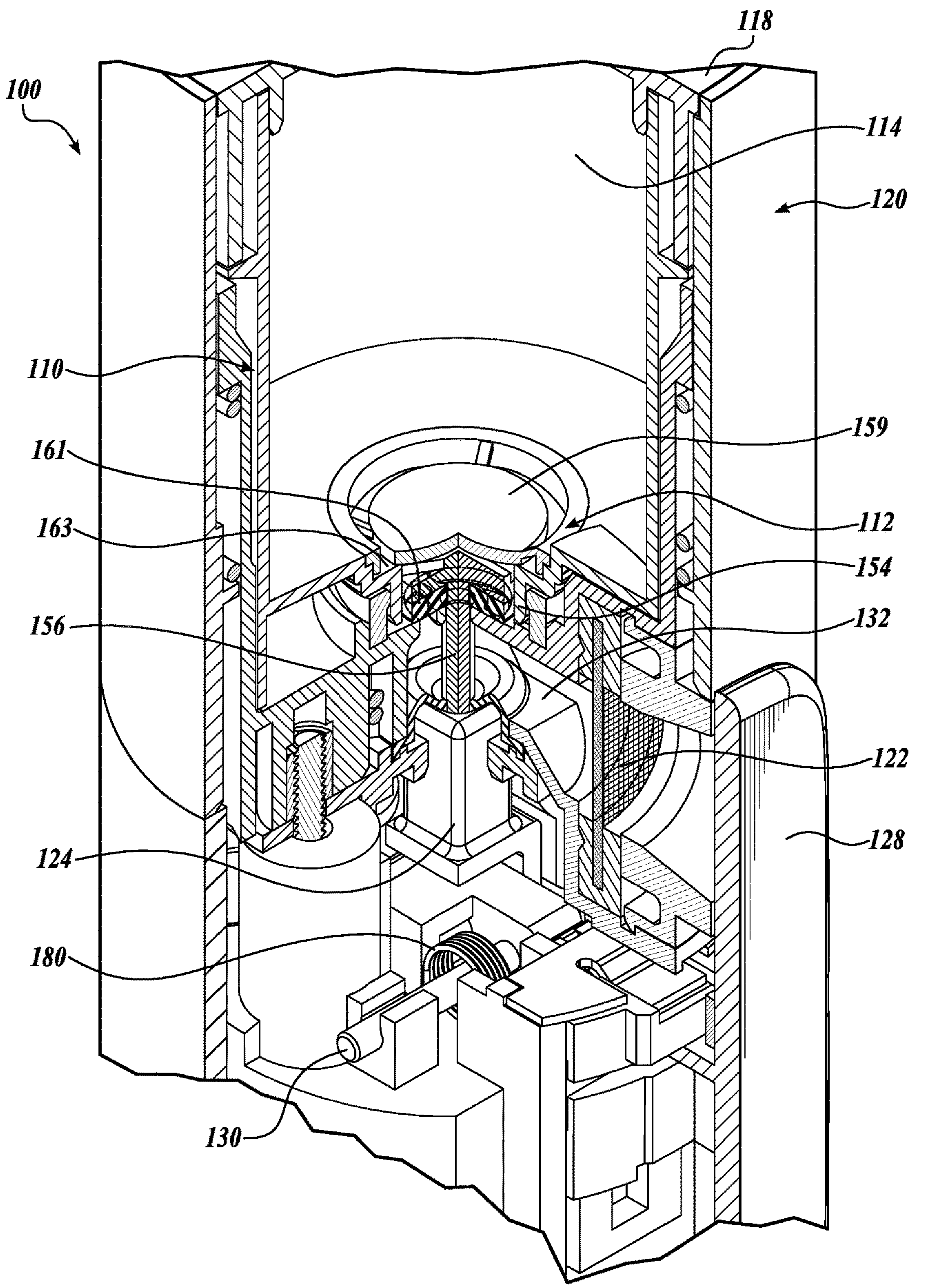
FIG. 1E is an isometric cutaway view of the system of FIG. 1A taken along lines 1E-1E in FIG. 1B.

For example, as illustrated in FIGS. 1D, 1E, 2B, and 2C, the nebulizing body 120 includes a switch 128 operatively coupled to a cam 126, which is, in turn, operatively coupled to a push rod 124. In this embodiment, the cam 126 pivots about pivot 130 against a biasing force of a spring 180. In an embodiment, the spring 180 biases the cam 126 into a first position in which the valve 112 in a closed position, as illustrated in FIGS. 1D and 1E. In use, as the switch 128 is selectively actuated via movement (e.g., linear movement, etc.), such as by the hand of a user, from the first position, as illustrated in FIGS. 1D and 1E, to a second position, as illustrated in FIGS. 2B and 2C, the cam 126 is rotated (in the direction of the arrow) against the biasing force of the spring 180. Rotation of the cam 126 causes the push rod 124 to be moved (e.g., linearly, etc.) to place the valve 112 in an open state. In this regard, the valve 112 is placed in an open state and the fluid reservoir 114 is coupled in fluid communication with the nebulizing assembly 122 when the switch 128 is activated, such as by the hand of a user. Removal of the hand of the user from the switch 128 allows the biasing force of the spring 180 to return the cam 126 and the switch 128 the non-engaged position (e.g., unactuated position, etc.) as shown in FIGS. 1D and 1E In an embodiment, when the switch 128 is activated the valve 112 is placed in an open state and the discharge aerosol circuitry (discussed further herein with respect to FIG. 5), which is operably coupled to the nebulizing assembly 122, is activated, thereby causing an aerosol A to be discharged from the system 100, as illustrated in FIGS. 2A, 2B, and 2C. As illustrated in FIG. 2C, in an embodiment, when the valve 112 in an open state, fluid in the fluid reservoir 114 is allowed to flow past valve seal 159 and into a space 132 that is disposed in fluid contact with the nebulizing assembly 122. In this regard, an aerosol A is discharged by the system 100 when the valve 112 is in an open state. This is in contrast to the embodiment illustrated in FIG. 1D, in which the valve seal 159 is shown disposed against the valve seat 163, thereby placing the valve 112 in a closed state. In an embodiment, element 161 forms part of a valve seal. In an embodiment, element 161 forms part of a valve stop.

In an embodiment, the system 100 includes an input assembly, such as input assembly 162 (see FIG. 5) in addition to switch 128. As discussed further herein with respect to FIG. 5, in an embodiment, the discharge aerosol circuitry is triggered (e.g., receive an input, electronically actuated, energized, etc.) to activate the nebulizing assembly 122 from the input assembly, thereby discharging aerosol A from system 100. In this regard, the fluid reservoir 114 is placed in fluid communication with the nebulizing assembly 122 through activation of the switch 128 and the nebulizing assembly 122 is activated in response to activation of the input assembly.

Figure 3A:
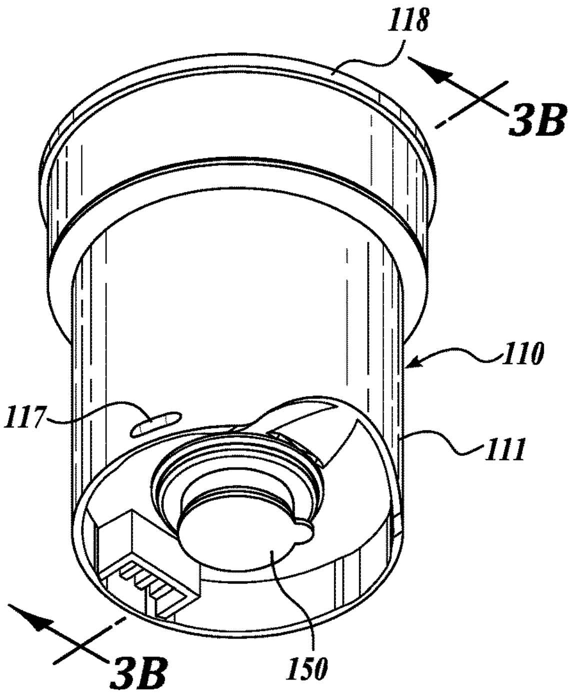
FIG. 3A is a perspective view of a replaceable cartridge in accordance with an embodiment of the disclosure.
Figure 3B:
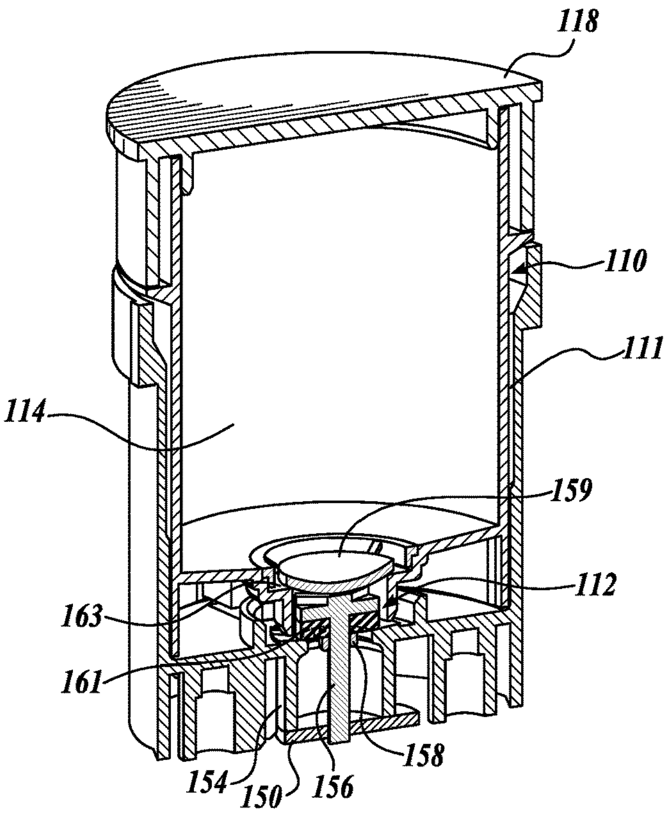
FIG. 3B is a cross-sectional view of the replaceable cartridge of FIG. 3A taken along the lines 3B-3B in FIG. 3A.

Referring to FIGS. 3A and 3B, the replaceable cartridge 110 including valve 112 is illustrated separately from the nebulizing body 120. The replaceable cartridge 110 is illustrated to include cartridge body 111 and a cartridge top 118, which, when coupled, define in part the fluid reservoir 114. In the illustrated embodiment, the valve 112 includes stop 161 coupled to shaft 156 and configured to limit the movement of shaft 156. In the illustrated embodiment, valve 112 also includes guide 158 slideably disposed around a portion of shaft 156 and configured to guide the movement of shaft 156 as it travels in opening and closing the valve 112. In FIGS. 3A and 3B, the replaceable cartridge 110 is shown to include protective seal 150, such a paper or plastic protective seal, configured to be removed by a user prior to use or punctured by coupling the removable cartridge 110 to the nebulizing body 120.

In operation, when the replaceable cartridge 110 is received by the nebulizing body 120 and, for example, the switch 128 has been activated (e.g., moved linearly, displaced, engaged, etc.), the push rod 124 displaces a valve seal 159 from the valve seat 163, thereby placing the valve 112 in an open state, as illustrated in FIG. 2C. Referring to FIG. 3A, the valve 112 is shown to include an annular ring 154 configured to cooperatively engage with nebulizing body 120 to provide a fluid-tight seal between the replaceable cartridge 110 and space 132 disposed within nebulizing body 120 (See FIG. 2C). In this regard, the valve 112 is configured to direct any fluid in the fluid reservoir 114 to the nebulizing assembly 122. Further, when the replaceable cartridge 110 is engaged with and received by the nebulizing body 120 and, accordingly, the valve 112 is an open state, fluid from the replaceable cartridge 110 is prevented from entering other portions of the nebulizing body 120.

It will be appreciated that valve 112 can be any valve configured to selectively place fluid reservoir 114 in fluid communication with nebulizing assembly 122 when the replaceable cartridge 110 is received by and engaged with the nebulizing body 120. In an embodiment, the valve 112 operates as a one-way valve, such as a check valve. In an embodiment, the check valve can be of the ball type, the diaphragm type, or of the swing type. In an embodiment, valve 112 is a two-way valve.

In an embodiment, the replaceable cartridge 110 includes a fluid disposed in the fluid reservoir 114. In an embodiment, the replaceable cartridge 110 includes a cosmetic or dermatological formulation disposed in the fluid reservoir 114. In an embodiment, the cosmetic or dermatological formulation includes a composition chosen from a foundation, a perfume, a moisturizer, a self-tanning agent, a lotion for the body or the face, a composition containing a hair agent, a sunscreen composition, and combinations thereof, among others.

In an embodiment, the system 100 includes two or more replaceable cartridges 110 each configured to be received by and engage with the nebulizing body 120. In an embodiment, each of the two or more replaceable cartridges 110 includes an identifier 116 configured to emit an input for receipt by cartridge identification circuitry (See FIG. 5). The input is indicative of the formulation disposed in the respective fluid reservoirs 114.

Figure 4:
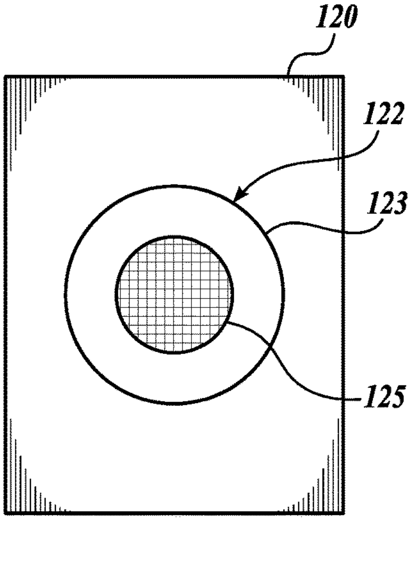
FIG. 4 is an illustration of an electro-mechanical nebulizing assembly in accordance with an embodiment of the disclosure.

Referring to FIG. 4, a nebulizing assembly 122 formed in accordance with an exemplary embodiment of the present disclosure and configured for use with system 100 will now be described in detail. As noted above, the nebulizing assembly 122 is configured to produce on-demand aerosol. The terms "nebulize," "nebulizing," etc., should be construed to include atomizing, misting, generating an aerosol, reducing to fine particles or spray, etc.

As shown in FIG. 4, the nebulizing assembly 122 generally includes at least one electro-mechanical nebulizing element 123, such as a piezoelectric element, fluidically coupled to the fluid reservoir 114 (FIG. 1D) when the valve 112 is in an open state and configured to discharge an aerosol (See FIGS. 2A-2C). In an embodiment, the nebulizing assembly 122 includes a mesh 125, such as a metallic mesh, disposed adjacent to the electro-mechanical nebulizing element 123, which receives a fluid from the fluid reservoir 114 of the replaceable cartridge 112. In the illustrated embodiment, the electro-mechanical nebulizing element 123 concentrically surrounds the mesh 125. In an embodiment, the nebulizing assembly 122 is a vibrating mesh dispenser assembly including a mesh 125 including apertures that is concentrically surrounded by the electro-mechanical nebulizing element 123. In an embodiment, the nebulizing assembly 122 is configured to discharge an aerosol including particles having an average diameter of less than 100 nm.

In an embodiment, the nebulizing assembly 122 is received within the replaceable cartridge 110. In an embodiment, the nebulizing assembly 122 is received within the nebulizing body 120. In an embodiment, the nebulizing assembly 122 includes replaceable nebulizing elements 123.

In an embodiment, during use, the electro-mechanical nebulizing element 123 contracts and expands upon the application of an alternating electric current, and consequently, the electro-mechanical nebulizing element 123 vibrates. When a liquid, such as a formulation from the fluid reservoir 114 of the replaceable cartridge 110, is in contact with the vibrating mesh 125, pressure builds in the vicinity of the mesh 125, creating a pumping action that extrudes the formulation through the apertures. When the mesh 125 vibrates at a sufficient frequency and with sufficient power, an aerosol A is formed from the formulation, which is emitted from the system 100 through mesh 125.

In an embodiment, the system 100 includes suitable circuitry for identifying one or more replaceable cartridges 110 received by the nebulizing body 120 and suitable circuitry for sending at least one output signal indicative of the identified replaceable cartridge(s) 110 for controlling and/or activating the nebulizing assembly 122. In that regard, attention is directed back to FIG. 2B, where a system 100 including circuitry for identifying one or more replaceable cartridges in accordance with embodiments of the present disclosure is illustrated. In the illustrated embodiment, replaceable cartridge 110 includes an identifier 116. The nebulizing body 120 includes cartridge identification assembly 172 (not shown in FIG. 2B). As discussed further herein with respect to FIG. 5, in certain embodiments the identifier 116 includes circuitry configured to generate one or more inputs for receipt by the cartridge identification circuitry disposed within the cartridge identification assembly 172.

Figure 5:
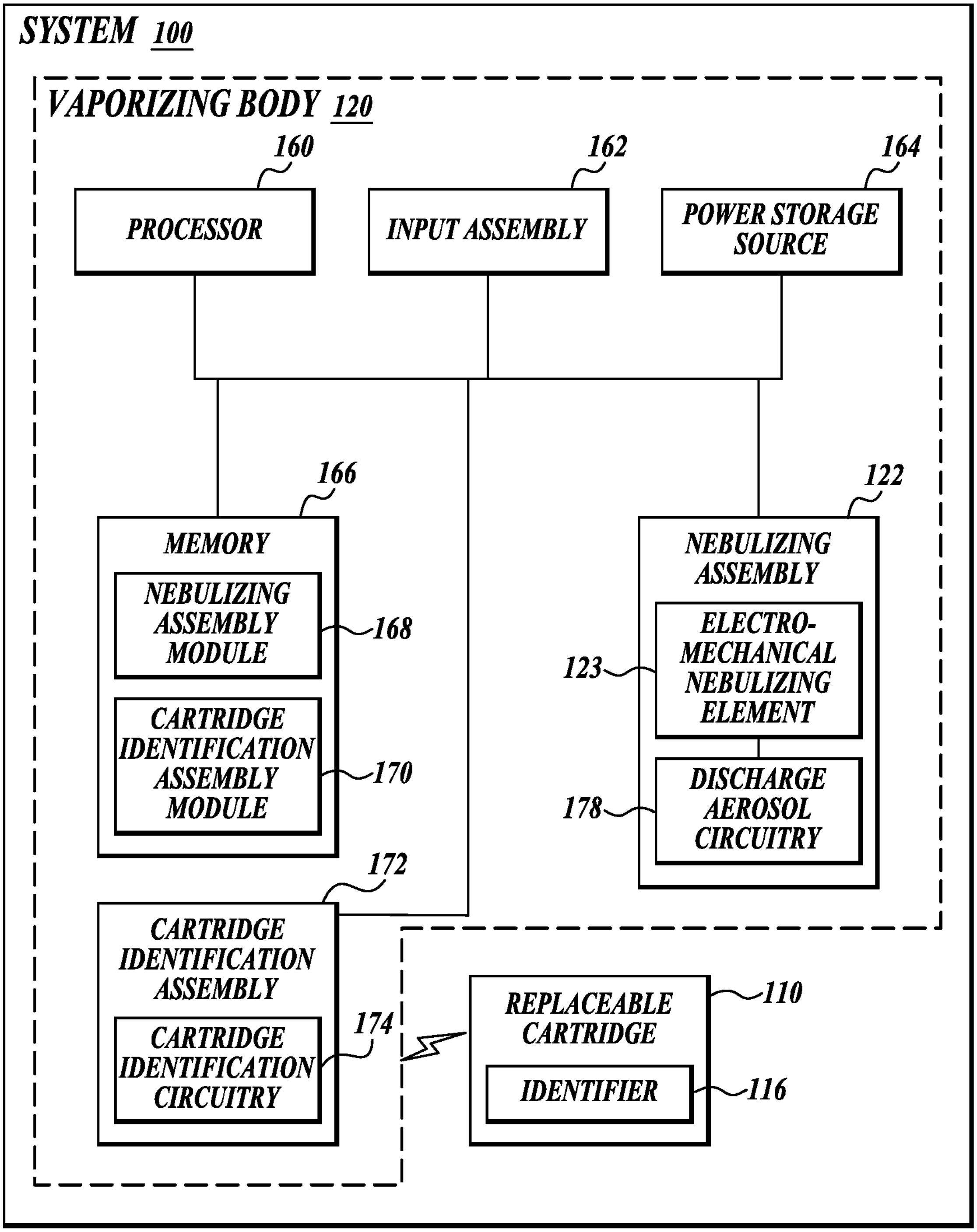
FIG. 5 is a block diagrammatic illustration of the internal operating structure of the system of FIG. 1A and its associated internal assemblies in accordance with an embodiment of the disclosure.

An embodiment of the internal operating structure of the system 100 and its associated internal assemblies is shown in block diagrammatic form in FIG. 5. An exemplary operating structure of the system 100 includes a programmed microcontroller or processor 160 configured to control the delivery of power to the nebulizing assembly 122 from the power storage source 164. Further, the processor 160 is configured to operate in accordance with program instructions stored in memory 166 or otherwise stored in hardware format for controlling aspects of the nebulizing assembly 122.

In the embodiment shown, the nebulizing assembly 122 includes discharge aerosol circuitry 178 operably coupled to the electro-mechanical nebulizing element 123 and configured to activate the electro-mechanical nebulizing element 123 to generate a discharge aerosol A (See FIGS. 2A-2C). In one embodiment, the electro-mechanical nebulizing element 123 includes a piezoelectric element that defines part of the nebulizing assembly 122. The discharge aerosol circuitry 178 is configured to activate the nebulizing assembly 122 in response to inputs received from the processor 160, inputs received from one or more modules stored in the memory 166, such as the nebulizing assembly module 168 and the cartridge identification assembly module 170, and/or inputs received from other assemblies (such as the input assembly 162 and the identifier 116). In an embodiment the nebulizing assembly module 168 and the cartridge identification assembly module 170 includes any suitable programs, files, or instructions for activating and controlling the nebulizing assembly 122.

The discharge aerosol circuitry 178 can be configured to receive input from an input assembly 162 (which may include an on/off button, a power adjust button, a mode control button, a nebulizing button, etc.). In an embodiment, the input assembly 162 is configured and arranged to selectively deliver power from the power storage source 164 to the nebulizing assembly 122, thereby generating aerosol A.

In an embodiment, the system 100 includes discharge aerosol circuitry 178 operably coupled to the nebulizing assembly 122 and configured to generate a discharge aerosol A responsive to one or more inputs indicative of a replaceable cartridge 110 identification. In this regard, in an embodiment, the system 100 includes a cartridge identification assembly 172 including cartridge identification circuitry 174, operably coupled to the discharge aerosol circuitry 178. In this regard, the cartridge identification assembly 172 is configured to receive one or more inputs from an identifier 116 carried by the replaceable cartridge 110 and to generate the one or more inputs indicative of a replaceable cartridge 110 identification for receipt by the cartridge identification circuitry 174.

In an embodiment, the one or more inputs indicative of a replaceable cartridge 110 identification correspond to a fluid disposed in the fluid reservoir 114, and wherein the discharge aerosol circuitry 178 is configured to operate the nebulizing assembly 122 based on the fluid disposed in the fluid reservoir 114. In this regard, in an embodiment, the system 100 is configured to operate the nebulizing assembly 122 based on, for example, a viscosity of a formulation disposed in the fluid reservoir 114. For example, an embodiment, the nebulizing assembly module 168 includes instructions configured to control the delivery of power to the nebulizing assembly 122 from the power storage source 164 controlling an oscillation frequency and an oscillation amplitude of the electro-mechanical nebulizing element 123 tailored to the viscosity of the particular fluid in the fluid reservoir 114. In this regard, sufficient power is provided to the nebulizing assembly 122 to nebulize the formulation and emit an aerosol A from the system 100.

In an embodiment, the cartridge identification assembly 172 is operatively coupled to the replaceable cartridge 110 by one or more of a wired connection or a wireless connection. In an embodiment, the wireless connection is a direct wireless connection, such as a Bluetooth connection, a near field communication (NFC) connection, a direct WiFi connection, or any other direct wireless connection. In an embodiment, the cartridge identification circuitry 174 includes one of a reader of a radio-frequency identification device and a near-field communications initiator and the replaceable cartridge 110 includes corresponding circuitry configured to communicate with the cartridge identification circuitry 174.

In an embodiment, the identifier 116 includes a portion configured to couple with the cartridge identification circuitry 174 having an electrical resistance indicative of the replaceable cartridge 110. In an embodiment, the identifier 116 includes one or more mechanical features indicative of the replaceable cartridge 110 and configured to engage with one or more switches included in the cartridge identification circuitry 174.

Certain embodiments disclosed herein utilize circuitry in order to implement treatment protocols, operably couple two or more components, generate information, determine operation conditions, control an appliance or method, process signals, and/or the like. Circuitry of any type can be used. In an embodiment, circuitry includes, among other things, one or more computing devices such as a processor (e.g., a microprocessor), a central processing unit (CPU), a digital signal processor (DSP), an application-specific integrated circuit (ASIC), a field-programmable gate array (FPGA), or the like, or any combinations thereof, and can include discrete digital or analog circuit elements or electronics, or combinations thereof. In an embodiment, circuitry includes one or more ASICs having a plurality of predefined logic components. In an embodiment, circuitry includes one or more FPGA having a plurality of programmable logic components.

In an embodiment, circuitry includes hardware circuit implementations (e.g., implementations in analog circuitry, implementations in digital circuitry, and the like, and combinations thereof). In an embodiment, circuitry includes combinations of circuits and computer program products having software or firmware instructions stored on one or more computer readable memories that work together to cause a device to perform one or more methodologies or technologies described herein. In an embodiment, circuitry includes circuits, such as, for example, microprocessors or portions of microprocessor, that require software, firmware, and the like for operation. In an embodiment, circuitry includes an implementation comprising one or more processors or portions thereof and accompanying software, firmware, hardware, and the like. In an embodiment, circuitry includes a baseband integrated circuit or applications processor integrated circuit or a similar integrated circuit in a server, a cellular network device, other network device, or other computing device. In an embodiment, circuitry includes one or more remotely located components. In an embodiment, remotely located components are operably coupled via wireless communication. In an embodiment, remotely located components are operably coupled via one or more receivers, transmitters, transceivers, or the like.

In an embodiment, circuitry includes one or more memory devices that, for example, store instructions or data. Non-limiting examples of one or more memory devices include volatile memory (e.g., Random Access Memory (RAM), Dynamic Random Access Memory (DRAM), or the like), non-volatile memory (e.g., Read-Only Memory (ROM), Electrically Erasable Programmable Read-Only Memory (EEPROM), Compact Disc Read-Only Memory (CD-ROM), or the like), persistent memory, or the like. Further non-limiting examples of one or more memory devices include Erasable Programmable Read-Only Memory (EPROM), flash memory, or the like. The one or more memory devices can be coupled to, for example, one or more computing devices by one or more instructions, data, or power buses.

In an embodiment, circuitry of the system 100 includes a computer-readable media drive or memory slot configured to accept signal-bearing medium (e.g., computer-readable memory media, computer-readable recording media, or the like). In an embodiment, a program for causing a system to execute any of the disclosed methods can be stored on, for example, a computer-readable recording medium (CRMM), a signal-bearing medium, or the like. Non-limiting examples of signal-bearing media include a recordable type medium such as any form of flash memory, magnetic tape, floppy disk, a hard disk drive, a Compact Disc (CD), a Digital Video Disk (DVD), Blu-Ray Disc, a digital tape, a computer memory, or the like, as well as transmission type medium such as a digital and/or an analog communication medium (e.g., a fiber optic cable, a waveguide, a wired communications link, a wireless communication link (e.g., transmitter, receiver, transceiver, transmission logic, reception logic, etc.). Further non-limiting examples of signal-bearing media include, but are not limited to, DVD-ROM, DVD-RAM, DVD+RW, DVD-RW, DVD-R, DVD+R, CD-ROM, Super Audio CD, CD-R, CD+R, CD+RW, CD-RW, Video Compact Discs, Super Video Discs, flash memory, magnetic tape, magneto-optic disk, MINIDISC, non-volatile memory card, EEPROM, optical disk, optical storage, RAM, ROM, system memory, web server, or the like.

It should be noted that for purposes of this disclosure, terminology such as "upper," "lower," "vertical," "horizontal," "inwardly," "outwardly," "inner," "outer," "front,"

"rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings. The term "about" means plus or minus 5% of the stated value.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A system comprising: a nebulizing body including at least one electro-mechanical nebulizing element; and a replaceable cartridge including one or more fluid reservoirs and a valve in fluid communication with the one or more fluid reservoirs, wherein the nebulizing body is configured to releaseably receive the replaceable cartridge without engaging with the replaceable cartridge, and wherein the nebulizing body includes a switch configured to selectively engage the replaceable cartridge when the replaceable cartridge is releaseably received by the nebulizing body, thereby placing the valve in an open state, wherein the nebulizing body and the replaceable cartridge are cooperatively configured such that the replaceable cartridge can be releaseably received by and engaged with the nebulizing body after having been previously releaseably received by and engaged with the nebulizing body.

2. The system of claim 1, wherein the valve is in an open state and the one or more fluid reservoirs are coupled in fluid communication with the at least one electro-mechanical nebulizing element when the replaceable cartridge is received by and engaged with the nebulizing body.

3. The system of claim 1, wherein the valve is in a closed state and the one or more fluid reservoirs are not coupled in fluid communication with the at least one electro-mechanical nebulizing element in an unengaged configuration.

4. The system of claim 1, further comprising a discharge aerosol circuitry operably coupled to the at least one electro-mechanical nebulizing element and configured to generate a discharge aerosol responsive to one or more inputs indicative of a replaceable cartridge identification.

5. The system of claim 4, further comprising a cartridge identification circuitry operably coupled to the discharge aerosol circuitry, the cartridge identification circuitry configured to receive one or more inputs from an identifier carried by the replaceable cartridge and to generate the one or more inputs indicative of a replaceable cartridge identification for receipt by the aerosol discharge circuitry.

6. The system of claim 5, wherein the cartridge identification circuitry includes one of a reader of a radio-frequency identification device and a near-field communications initiator.

7. The system of claim 5, wherein the replaceable cartridge includes the identifier configured to receive one or more inputs from the cartridge identification circuitry and generate the one or more inputs indicative of a replaceable cartridge identification for receipt by the cartridge identification circuitry.

8. The system of claim 5, wherein the identifier includes a portion configured to couple with the cartridge identification circuitry having an electrical resistance indicative of the replaceable cartridge.

9. The system of claim 5, wherein the identifier includes one or more mechanical features indicative of the replaceable cartridge configured to engage with one or more switches included in the cartridge identification circuitry.

10. The system of claim 4, wherein the one or more inputs indicative of a replaceable cartridge identification corresponds to one or more fluids disposed in the one or more fluid reservoirs, and wherein the discharge aerosol circuitry is configured to operate the at least one electro-mechanical nebulizing element based on the one or more fluids disposed in the one or more fluid reservoirs.

11. The system of claim 4, wherein the replaceable cartridge is a first replaceable cartridge, the system further comprising a second replaceable cartridge including one or more fluid reservoirs and configured to be releaseably received by the nebulizing body; a valve in fluid communication with the one or more fluid reservoirs; and a second identifier configured to generate one or more inputs indicative of a second replaceable cartridge identification.

12. The system of claim 11, wherein the one or more inputs indicative of the second replaceable cartridge identification correspond to one or more fluids disposed in the one or more fluid reservoirs of the second replaceable cartridge, and wherein the discharge aerosol circuitry is configured to operate the at least one electro-mechanical nebulizing element based on the one or more fluids disposed in the one or more fluid reservoirs of the second replaceable cartridge.

13. The system of claim 1, wherein the replaceable cartridge includes a cosmetic or dermatological composition disposed in the one or more fluid reservoirs.

14. The system of claim 1, wherein the at least one electro-mechanical nebulizing element includes a piezoelectric element configured to be in fluid communication with the one or more fluid reservoirs of the replaceable cartridge when the valve is in an open state.

15. The system of claim 14, wherein the at least one electro-mechanical nebulizing element further includes a mesh disposed adjacent to the piezoelectric element and separated from the piezoelectric element by a space configured to receive a fluid from the one or more fluid reservoirs of the replaceable cartridge.

16. The system of claim 1, wherein the at least one electro-mechanical nebulizing element is configured to discharge an aerosol including particles having an average diameter of less than 100 μm.

17. The system of claim 14, further comprising a discharge aerosol circuitry operably coupled to the at least one electro-mechanical nebulizing element including the piezoelectric element and configured to apply an electrical field to the piezoelectric element, the electrical field having a frequency and an amplitude responsive to one or more inputs indicative of a replaceable cartridge identification.

18. The system of claim 1, wherein the valve maintains a closed state when replaceable cartridge is not engaged with the nebulizing body.

* * * * *